United States Patent
Furukawa et al.

(10) Patent No.: US 10,604,658 B2
(45) Date of Patent: Mar. 31, 2020

(54) ORGANIC SILICON COMPOUND, SURFACE TREATMENT AGENT CONTAINING SAME, RESIN COMPOSITION CONTAINING SAME, AND GEL OR CURED PRODUCT OF SAME

(71) Applicant: Dow Corning Toray Co., Ltd., Tokyo (JP)

(72) Inventors: Haruhiko Furukawa, Chiba (JP); Makoto Iwai, Chiba (JP); Kousei Iwakawa, Chiba (JP); Eiji Kitaura, Chiba (JP); Kazuhiro Nishijima, Chiba (JP); Tadashi Okawa, Chiba (JP)

(73) Assignee: Dow Toray Co., Ltd., Tokyo (JP)

( * ) Notice: Subject to any disclaimer, the term of this patent is extended or adjusted under 35 U.S.C. 154(b) by 546 days.

(21) Appl. No.: 15/757,702

(22) PCT Filed: Aug. 11, 2014

(86) PCT No.: PCT/JP2014/071510
§ 371 (c)(1),
(2) Date: Mar. 6, 2018

(87) PCT Pub. No.: WO2015/022998
PCT Pub. Date: Feb. 19, 2015

(65) Prior Publication Data
US 2018/0230172 A1  Aug. 16, 2018

(30) Foreign Application Priority Data
Aug. 14, 2013 (JP) ................................. 2013-168661

(51) Int. Cl.
| | | |
|---|---|---|
| *C09C 3/12* | (2006.01) | |
| *C07F 7/18* | (2006.01) | |
| *C08K 9/06* | (2006.01) | |
| *C08G 77/50* | (2006.01) | |
| *C09D 183/14* | (2006.01) | |
| *C08G 77/48* | (2006.01) | |
| *C08K 3/22* | (2006.01) | |
| *C08K 5/5419* | (2006.01) | |
| *C09K 5/02* | (2006.01) | |
| *C08G 77/12* | (2006.01) | |
| *C08G 77/18* | (2006.01) | |
| *C08G 77/20* | (2006.01) | |

(52) U.S. Cl.
CPC .............. *C09C 3/12* (2013.01); *C07F 7/1804* (2013.01); *C08G 77/485* (2013.01); *C08G 77/50* (2013.01); *C08K 3/22* (2013.01); *C08K 5/5419* (2013.01); *C08K 9/06* (2013.01); *C09D 183/14* (2013.01); *C09K 5/02* (2013.01); *C08G 77/12* (2013.01); *C08G 77/18* (2013.01); *C08G 77/20* (2013.01); *C08K 2003/2227* (2013.01); *C08K 2201/001* (2013.01); *C08K 2201/003* (2013.01)

(58) Field of Classification Search
CPC ....................................................... C09C 3/12
See application file for complete search history.

(56) References Cited

U.S. PATENT DOCUMENTS

| | | | |
|---|---|---|---|
| 3,885,984 A | 5/1975 | Wright | |
| 6,306,957 B1 | 10/2001 | Nakano et al. | |
| 6,380,301 B1 | 4/2002 | Enami et al. | |
| 2003/0120016 A1* | 6/2003 | Okawa | C08G 77/485 528/10 |

FOREIGN PATENT DOCUMENTS

| | | |
|---|---|---|
| JP | S50105573 A | 8/1975 |
| JP | S5155870 A | 5/1976 |
| JP | S61157587 A | 7/1986 |
| JP | H09316395 A | 12/1997 |
| JP | 2000256558 A | 9/2000 |
| JP | 2001139815 A | 5/2001 |
| JP | 2012052018 A | 3/2012 |

OTHER PUBLICATIONS

Machine translation of JP 9-316395 (no date).*
PCT/JP2014/071510 International Search Report dated Oct. 24, 2014, 2 pages.
English language abstract and machine translation for JPS5155870(A) extracted from http://worldwide.espacenet.com database on Apr. 9, 2018, 7 pages.
English language abstract and machine translation for JPS61157587(A) extracted from http://worldwide.espacenet.com database on Apr. 5, 2018, 6 pages.
English language abstract and machine translation for JPH09316395(A) extracted from http://worldwide.espacenet.com database on Apr. 9, 2018, 36 pages.
English language abstract and machine translation for JP2012052018(A) extracted from http://worldwide.espacenet.com database on Apr. 9, 2018, 28 pages.

* cited by examiner

*Primary Examiner* — Marc S Zimmer
(74) *Attorney, Agent, or Firm* — Warner Norcross + Judd LLP

(57) ABSTRACT

An organic silicon compound is disclosed which is represented by a formula: $(R^1_3SiO)_3SiR^2$—$[SiR^3_2O]_y[SiR^3_2]_w$—$R^4$—$R^5$, wherein each of $R^1$ and $R^3$ is a group independently selected from the group consisting of alkyl groups, alkenyl groups, aryl groups, aralkyl groups and alkoxy groups having 1 to 20 carbon atoms, $R^2$ is a divalent hydrocarbon group or an oxygen atom, $R^4$ is a divalent hydrocarbon group, or a direct bond to a silicon (Si) atom, $R^5$ is a monovalent group represented by $(R^6O)_qR^7_{(3-q)}Si$ or a monovalent hydrocarbon group having 1 to 20 carbon atoms, and each of $R^6$ and $R^7$ is a group independently selected from the group consisting of alkyl groups, alkenyl groups, aryl groups, aralkyl groups and alkoxy groups having 1 to 20 carbon atoms, and q is an integer between 1 and 3, y is an integer between 0 and 200, and w is 0 or 1.

19 Claims, No Drawings

ORGANIC SILICON COMPOUND, SURFACE TREATMENT AGENT CONTAINING SAME, RESIN COMPOSITION CONTAINING SAME, AND GEL OR CURED PRODUCT OF SAME

CROSS-REFERENCE TO RELATED APPLICATIONS

This application is the National Stage of International Application No. PCT/JP2014/071510 filed on 11 Aug. 2014, which claims priority to and all advantages of JP Patent Application No. 2013-168861 filed on 14 Aug. 2013, the content of which is hereby incorporated by reference.

TECHNICAL FIELD

The present invention relates to a novel organic silicon compound, a surface treatment agent containing this organic silicon compound, and a resin composition containing this organic silicon compound, and more specifically relates to a surface treatment agent for thermally conductive fillers which contains a novel organic silicon compound, and a thermally conductive silicone composition containing this organic silicon compound.

BACKGROUND ART

In cases where functional fillers selected from among thermally conductive fillers, fluorescent fillers, electrically conductive fillers, dielectric fillers, insulating fillers, light-diffusing fillers, translucent fillers, coloring fillers and reinforcing fillers are blended with resin compositions, it is possible to obtain greases, gels, cured rubbers, coating agents and phase change materials having a variety of functions, and such functional fillers are therefore widely used on an industrial scale. In particular, as electronic parts, such as transistors, ICs and memory elements, mounted on printed circuit boards and hybrid ICs have advanced in terms of density and integration in recent years, a variety of thermally conductive silicone compositions have been used in order to efficiently dissipate heat from these electronic parts. Thermally conductive silicone greases, thermally conductive silicone gel compositions and thermally conductive silicone rubber compositions are known as such thermally conductive silicone compositions.

For example, thermally conductive silicone compositions which contain a silicone oil as a primary component and which also contain an inorganic filler such as zinc oxide or an alumina powder (see Japanese Unexamined Patent Application Publication Nos. S50-105573, S51-55870 and S61-157587), a thermally conductive silicone composition consisting of an organopolysiloxane, an organopolysiloxane having an alkoxy group or acyloxy group bonded to a silicon atom, a thermally conductive filler and a curing agent (see Japanese Unexamined Patent Application Publication No. 2000-256558) and a thermally conductive silicone composition containing an organopolysiloxane, a curing agent and a thermally conductive filler that has been surface treated with a silaklylene-oligosiloxane having an alkoxy group bonded to a silicon atom (see Japanese Unexamined Patent Application Publication No. 2001-139815) have been proposed as such thermally conductive silicone compositions.

PRIOR ART DOCUMENTS

Patent Documents

Patent Document 1: Japanese Unexamined Patent Application Publication No. S50-105573
Patent Document 2: Japanese Unexamined Patent Application Publication No. S51-55870
Patent Document 3: Japanese Unexamined Patent Application Publication No. S61-157587
Patent Document 4: Japanese Unexamined Patent Application Publication No. 2000-256558
Patent Document 5: Japanese Unexamined Patent Application Publication No. 2001-139815

SUMMARY OF INVENTION

Technical Problem

Many components proposed as surface treatment agents in resin compositions containing functional fillers, and especially in the above-mentioned thermally conductive silicone compositions, are compounds having hydrolyzable groups such as alkoxysilyl groups. These hydrolyzable groups are somewhat effective for metal oxides having surface hydroxyl groups, such as alumina, but have no effect on fillers having no surface hydroxyl groups, such as boron nitride or graphite, and in cases where these functional fillers, and especially thermally conductive fillers, are highly packed, the viscosity of the obtained composition increases dramatically, meaning that handleability significantly deteriorates. Therefore, in the case of publicly known surface treatment agents containing organopolysiloxanes, because it is not possible to pack functional fillers in resin compositions at a high packing density, the performance of the obtained composition is insufficient or it is not possible to achieve both handleability and performance.

The present invention was developed mainly to solve the above-mentioned problems, and provides a novel organopolysiloxane which exhibits good handleability and dispersion stability and avoids problems such as thickening or dispersion even when a variety of functional fillers are blended at high quantities in a resin composition; a surface treatment agent containing this organic silicon compound; and a functional resin composition. In particular, the present invention provides a novel organic silicon compound which exhibits good handleability and high thermal conductivity even if a large quantity of a thermally conductive filler is incorporated in order to obtain a highly thermally conductive silicone composition; a surface treatment agent for thermally conductive fillers, which contains this organic compound; and a thermally conductive silicone composition which contains this organic silicon compound. Purpose of the present invention is not limited to the above examples.

Solution to Problem

The objectives of the present invention can be achieved by means of an organic silicon compound represented by a formula (1) below:

[Formula 1]

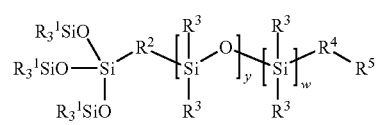

(1)

(wherein
each of $R^1$ and $R^3$ is a group selected independently from the group consisting of alkyl groups, alkenyl groups, aryl groups, aralkyl groups and alkoxy groups having 1 to 20 carbon atoms,
$R^2$ is a divalent hydrocarbon group, which may contain a hetero atom, or an oxygen atom,
$R^4$ is a divalent hydrocarbon group, which may contain a hetero atom, or a direct bond to a silicon (Si) atom,
$R^5$ is a monovalent group represented by $(R^6O)_q R^7_{(3-q)}Si$ or a monovalent hydrocarbon group having 1 to 20 carbon atoms, and each of $R^6$ and $R^7$ is a group independently selected from the group consisting of alkyl groups, alkenyl groups, aryl groups, aralkyl groups and alkoxy groups having 1 to 20 carbon atoms, and
q is an integer between 1 and 3, y is an integer between 0 and 200, and w is an integer that is 0 or 1)

It is preferable for each of the $R^1$ groups in the aforementioned formula (1) independently selected from an alkyl group having 1 to 20 carbon atoms. In addition, it is preferable for y to be an integer between 1 and 20.

In addition, the present invention also relates to a surface treatment agent that contains the aforementioned organic silicon compound represented by the formula (1).

The surface treatment agent of the present invention can be advantageously used to treat the surface of a variety of functional fillers, and in particular can be used to treat the surface of one or more types of filler selected from among thermally conductive fillers, fluorescent fillers, electrically conductive fillers, dielectric fillers, insulating fillers, light-diffusing fillers, translucent fillers, coloring fillers and reinforcing fillers.

A surface treatment agent containing the organic silicon compound of the present invention can be used to treat the surface of one or more types of filler selected from among inorganic fillers, organic fillers, nanocrystalline structures, quantum dots and fillers whose surfaces are partially or wholly coated by silica layers. Moreover, these surface treatment agents can be used when a variety of functional fillers is being synthesized.

The surface treatment agent of the present invention is preferably a surface treatment agent for a thermally conductive filler.

In addition, the present invention also relates to a resin composition that contains the aforementioned organic silicon compound and a filler whose surface has been treated with the aforementioned organic silicon compound. These resin compositions may be curable resin compositions, thermoplastic resin compositions, or non-curable or thickenable resin compositions.

The resin composition of the present invention can be used in a variety of applications, depending on the type of functional filler and resin, and can be particularly used in applications selected from among thermally conductive materials, electrically conductive materials, semiconductor sealing materials, optical materials, functional coating materials and cosmetic materials.

It is particularly preferable for the resin composition of the present invention to exhibit thickening properties, curing properties or phase change properties. Thickening properties means that the initial viscosity does not greatly change, but that the overall viscosity increases when the composition is heated under prescribed usage conditions or when a thickening agent is used, thereby obtaining a gel, viscous liquid or paste, and an example thereof is a grease composition or the like. Curing properties means that the composition is cured by means of heating and so on, and examples thereof include hard coat resin compositions, semiconductor sealing resin compositions, resin compositions able to be molded into sheets, resin compositions that has flexibility and are cured into soft gels, and semi-curable resin compositions that form soft rubbers having a degree of plasticity. Phase change properties means that when the functional filler is filled in a heat-softenable resin having a softening point, such as a wax, phase change occurs according to the operating temperature of a heat-dissipating electronic component or the like, and an example thereof is what is called phase change material.

Furthermore, the present invention also relates to a thermally conductive silicone composition that contains (A) the aforementioned organic silicon compound represented by the formula (1) and (B) a thermally conductive filler.

The silicone composition of the present invention may further contain (C) at least one type of organopolysiloxane other than the aforementioned organic silicon compound represented by the formula (1).

It is preferable for the aforementioned thermally conductive filler (B) to be at least one type of powder and/or fiber selected from the group consisting of a pure metal, an alloy, a metal oxide, a metal hydroxide, a metal nitride, a metal carbide, a metal silicide, carbon, a soft magnetic alloy and a ferrite.

In addition, the aforementioned pure metal is preferably bismuth, lead, tin, antimony, indium, cadmium, zinc, silver, copper, nickel, aluminum, iron or metallic silicon,
the aforementioned alloy is preferably an alloy consisting of two or more metals selected from the group consisting of bismuth, lead, tin, antimony, indium, cadmium, zinc, silver, copper, nickel, aluminum, iron and metallic silicon,
the aforementioned metal oxide is preferably alumina, zinc oxide, silicon oxide, magnesium oxide, beryllium oxide, chromium oxide or titanium oxide,
the aforementioned metal hydroxide is preferably magnesium hydroxide, aluminum hydroxide, barium hydroxide or calcium hydroxide,
the aforementioned metal nitride is preferably boron nitride, aluminum nitride or silicon nitride,
the aforementioned metal carbide is preferably silicon carbide, boron carbide or titanium carbide,
the aforementioned metal silicide is preferably magnesium silicide, titanium silicide, zirconium silicide, tantalum silicide, niobium silicide, chromium silicide, tungsten silicide or molybdenum silicide,
the aforementioned carbon is preferably diamond, graphite, a fullerene, carbon nanotubes, graphene, activated carbon or monolithic carbon black,
the aforementioned soft magnetic alloy is preferably an Fe—Si alloy, an Fe—Al alloy, an Fe—Si—Al alloy, an Fe—Si—Cr alloy, an Fe—Ni alloy, an Fe—Ni—Co alloy, an Fe—Ni—Mo alloy, an Fe—Co alloy, an Fe—Si—Al—Cr alloy, an Fe—Si—B alloy or an Fe—Si—Co—B alloy, and
the aforementioned ferrite is preferably a Mn—Zn ferrite, a Mn—Mg—Zn ferrite, a Mg—Cu—Zn ferrite, a Ni—Zn ferrite, a Ni—Cu—Zn ferrite or a Cu—Zn ferrite.

It is preferable for the aforementioned thermally conductive filler (B) to be (B1) a lamellar boron nitride powder having an average particle diameter of 0.1 to 30 μm, (B2) a granular boron nitride powder having an average particle diameter of 0.1 to 50 μm, (B3) a spherical and/or crushed aluminum oxide powder having an average particle diameter of 0.01 to 50 μm, (B4) a spherical and/or crushed graphite having an average particle diameter of 0.01 to 50 μm, or a mixture of two or more types thereof.

It is preferable for the content of the aforementioned component (B) to be 100 to 3,500 parts by mass relative to a total of 100 parts by mass of the aforementioned component (A) and the aforementioned component (C).

It is preferable for the organopolysiloxane of the aforementioned component (C) to have a hydrolyzable functional group bonded to a silicon atom in the molecule.

It is preferable for the aforementioned component (C) to be an organopolysiloxane having a monovalent hydrocarbon group having an aliphatic unsaturated bond bonded to a silicon atom in the molecule and an organopolysiloxane having a hydrogen atom bonded to a silicon atom in the molecule, and to further contain a catalyst that thickens or cures these organopolysiloxanes by means of a hydrosilylation reaction.

In addition, it is preferable for the aforementioned component (C) to be an organopolysiloxane having an aliphatic unsaturated bond bonded to a silicon atom in the molecule and having a monovalent hydrocarbon group having an aliphatic unsaturated bond bonded to a silicon atom and an organopolysiloxane having a hydrogen atom bonded to a silicon atom in the molecule, and to further contain a catalyst that thickens or cures these organopolysiloxanes by means of a hydrosilylation reaction.

In addition, the present invention also relates to a gel or cured product obtained by thickening or curing the aforementioned thermally conductive silicone composition, which contains a thickening or curing catalyst, by means of a hydrosilylation reaction.

Advantageous Effects of Invention

The novel organic silicon compound according to the present invention is useful as a surface treatment agent for a variety of functional fillers, and has the advantage of blending large quantities of a variety of functional fillers in resin compositions without losing handleability or dispersion stability. In particular, the novel organic silicon compound according to the present invention is useful for surface treating thermally conductive fillers, the thermally conductive silicone composition of the present invention exhibits ease of handing without increasing viscosity of the composition even when a large quantity of a thermally conductive filler is blended in order to obtain a highly thermally conductive silicone composition, and in the case of a curable composition, the cured product becomes homegenious.

DESCRIPTION OF EMBODIMENTS

Firstly, a detailed explanation will be given of an organic silicon compound which is the novel organic silicon compound according to the present invention, which is contained in the surface treatment agent of the present invention and which is disclosed as the component (A) in the resin composition of the present invention (which is preferably a thermally conductive silicone composition).

The organic silicon compound of the present invention is an organic silicon compound represented by the formula (1):

[Formula 2]

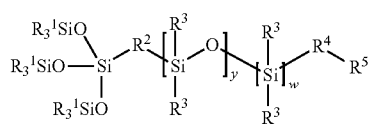

(1)

In the formula (1), each of $R^1$ and $R^3$ is a group independently selected from the group consisting of alkyl groups, alkenyl groups, aryl groups, aralkyl groups and alkoxy groups having 1 to 20 carbon atoms. Specific examples thereof include straight chain alkyl groups such as methyl groups, ethyl groups, propyl groups, butyl groups, pentyl groups, hexyl groups, heptyl groups, octyl groups, nonyl groups, decyl groups, undecyl groups, dodecyl groups, tridecyl groups, tetradecyl groups, pentadecyl groups, hexadecyl groups, heptadecyl groups, octadecyl groups, nonadecyl groups and eicosyl groups; branched-chain alkyl groups such as 2-methylundecyl groups and 1-hexylheptyl groups; cyclic alkyl groups such as cyclododecyl groups; hydrocarbon groups having an unsaturated bond, such as vinyl groups, allyl groups, butenyl groups, hexenyl groups and octenyl groups; aryl groups such as phenyl groups, tolyl groups and xylyl groups; aralkyl groups such as benzyl groups, phenethyl groups and 2-(2,4,6-trimethylphenyl)propyl groups; and alkoxy groups such as methoxy groups, ethoxy groups, n-propoxy groups and iso-propoxy groups.

In the formula (1), $R^2$ is a divalent hydrocarbon group, which may contain a hetero atom, or an oxygen atom, and in the case of a divalent hydrocarbon group, the hetero atom may be an oxygen atom or a sulfur atom. It is preferable for $R^2$ to be a divalent hydrocarbon group having 1 to 20 carbon atoms or an oxygen atom, or a divalent hydrocarbon group having 1 to 20 carbon atoms and containing 1 to 2 oxygen atoms, examples of which include the divalent linking groups represented by the structural formulae shown below and an oxygen atom (—O—).

[Formula 3]

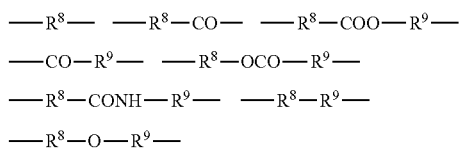

In the formulae, "CO" is a carbonyl group represented by —C(=O)—, the $R^8$ groups each are independently a substituted or unsubstituted straight chain or branched chain alkylene or alkenylene group having 2 to 22 carbon atoms or an arylene groups having 6 to 22 carbon atoms. In addition, the $R^9$ groups are either the same as the $R^8$ groups or are groups selected from among divalent groups represented by the formulae below.

[Formula 4]

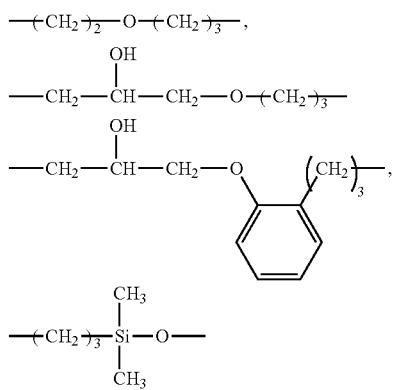

-continued

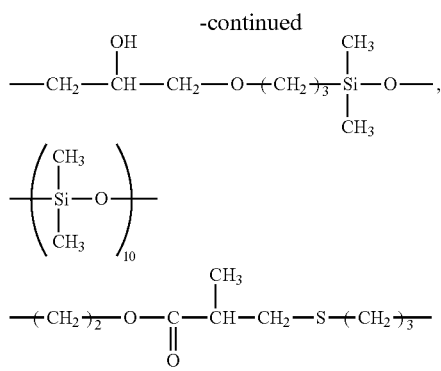

Specifically, $R^2$ is a group selected from among a methylene group, an ethylene group, a methylmethylene group, a propylene group, a methylethylene group, a butylene group, a phenylene group, a methylenephenylmethyl group, an ethylenephenethyl group, an oxygen atom, a methylene ether group, an ethylene ether group, a propylene ether group, a butylene ether group, a phenyl ether group, a phenylcarbonyl group, a carbonyl ether group, an oxycarbonyl group, a methylenecarbonyl group, an ethylenecarbonyl group, a propylenecarbonyl group, an ethylenecarboxylpropyl group and a (methyl)ethylenecarboxylpropyl group. From the perspectives of ease of procurement of raw materials and ease of synthesis, it is particularly preferable for $R^2$ to be a methylene group, an ethylene group, a methylmethylene group, a propylene group, a methylethylene group, an oxygen atom, an oxymethylene group, an oxyethylene group, an ethylenecarboxylpropyl group or a (methyl)ethylenecarboxylpropyl group.

In the formula (1), $R^4$ is a divalent hydrocarbon group, which may contain a hetero atom, or a direct bond to a silicon (Si) atom, and can be, for example, a group formed by an addition reaction of a silicon-bonded hydrogen atom to a functional group having a terminal unsaturated hydrocarbon group such as an alkenyl group, an acyloxy group or a methacryloxy group, or a group formed by a reaction between a silanol group and a hydrolyzable functional group such as a halogen atom, an alkoxy group or an acyloxy group. These structures are, for example, divalent linking groups represented by the structural formulae below or direct bonds to a silicon atom. In the formulae, CO, $R^6$ and $R^9$ are synonymous with those mentioned above.

[Formula 5]

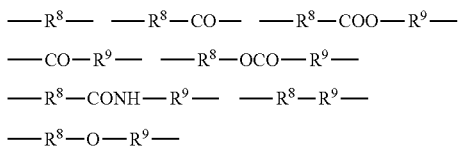

Specifically, $R^4$ is a group selected from among a methylene group, an ethylene group, a methylmethylene group, a propylene group, a methylethylene group, a butylene group, a phenylene group, a methylenephenylmethyl group, an ethylenephenethyl group, an oxygen atom, a methylene ether group, an ethylene ether group, a propylene ether group, a butylene ether group, a phenyl ether group, a phenylcarbonyl group, a carbonyl ether group, an oxycarbonyl group, a methylenecarbonyl group, an ethylenecarbonyl group, a propylenecarbonyl group, an ethylenecarboxylpropyl group and a (methyl)ethylenecarboxylpropyl group. From the perspectives of ease of procurement of raw materials and ease of synthesis, it is particularly preferable for $R^4$ to be a methylene group, an ethylene group, a methylmethylene group, a propylene group, a methylethylene group, an oxygen atom, an oxymethylene group, an oxyethylene group, an ethylenecarboxylpropyl group or a (methyl)ethylenecarboxylpropyl group.

In the formula (1), $R^5$ is a monovalent group represented by $(R^6O)_qR^7_{(3-q)}Si$ or a monovalent hydrocarbon group having 1 to 20 carbon atoms. The monovalent hydrocarbon group having 1 to 20 carbon atoms can be, for example, can be a group selected from among the group consisting of the aforementioned alkyl groups, alkenyl groups, aryl groups, aralkyl groups and alkoxy groups having 1 to 20 carbon atoms, some of the hydrogen atoms bonded to carbon atoms can be substituted with halogen atoms such as fluorine atoms, amino groups, carboxyl groups, and so on, and the monovalent hydrocarbon group having 1 to 20 carbon atoms can be straight chain or partially branched chain. It is particularly preferable for $R^5$ to be an aryl group having 6 to 20 carbon atoms. It is preferable for the aryl group to have a plurality of aromatic rings, and the aryl group may be condensed. It is more preferable for $R^5$ to be an aryl group having 10 to 20 carbon atoms and having a plurality of aromatic rings. Examples of this type of aryl group having 10 to 20 carbon atoms and having a plurality of aromatic rings include naphthyl groups, alkylnaphthyl groups, anthracenyl groups, biphenyl groups, phenylnaphthyl groups, phenylanthracenyl groups, phenylphenanthrenyl groups, phenylpyrenyl groups, terphenylene groups, phenylterphenylene groups, alkylbiphenyl groups, carbonylbiphenyl groups, alkoxyalkylbiphenyl groups, alkoxynaphthyl groups, acyloxynaphthyl groups, alkoxycarbonylnaphthyl groups, alkyl ether naphthyl groups, phenoxyphenyl groups and phenylcarbonyloxyphenyl groups. Preferred aryl groups are 1-naphthyl groups, 2-naphthyl groups, o-biphenyl groups, m-biphenyl groups, p-biphenyl groups, p-biphenyl ether groups, p-methylnaphthyl groups and p-ethylnaphthyl groups. Particularly preferred aryl groups are 1-naphthyl groups and 2-naphthyl groups.

$R^6$ and $R^7$ each are independently a group selected from the group consisting of alkyl groups, alkenyl groups, aryl groups, aralkyl groups and alkoxy groups having 1 to 20 carbon atoms, examples of which are the same as those listed above. q is an integer between 1 and 3, y is an integer between 0 and 200, and w is an integer that is 0 or 1.

In the formula (1), the $R^1$ groups each are preferably and independently an alkyl group having 1 to 20 carbon atoms, and more preferably an alkyl group having 1 to 10 carbon atoms. For example, the $R^1$ groups can be methyl groups, ethyl groups, n-propyl groups, isopropyl groups, butyl groups, t-butyl groups, pentyl groups, hexyl groups, or the like. Methyl groups are particularly preferred as the $R^1$ groups.

In the formula (1), y is preferably an integer between 1 and 100, and more preferably an integer between 1 and 20.

The organic silicon compound (A), which is contained as a component of the present invention, contains a trialkylsilyl group, and therefore hardly gels and exhibits excellent thermal stability when used as a treatment agent for a variety of functional fillers, and especially for thermally conductive fillers. In addition, in cases where the organic silicon component (A) is used as a matrix material, it is possible to obtain a resin composition, and especially a thermally conductive composition, having a relatively low viscosity and excellent handleability.

In addition, the organic silicon compound (A), which is contained as a component of the present invention, contains an alkoxysilyl group, and therefore hardly gels and exhibits excellent thermal stability when used as a treatment agent for a variety of functional fillers, and especially for thermally conductive fillers. In addition, when the organic silicon compound (A) has a functional group that contains a plurality of aromatic rings, affinity for a filler having a lamellar structure or a filler consisting of a polycyclic aromatic compound is high, and in cases where a composite material such as a grease, a compound or a gel is produced by using the organic silicon compound in a surface treatment agent or a base oil, miscibility is good and it is possible to suppress an increase in viscosity. Furthermore, it is possible to achieve an increase in functionality, such as an increase in refractive index.

The method for producing the organic silicon compound (A) used in the present invention is not particularly limited, but it is possible to obtain the organic silicon compound by, for example, subjecting an organosiloxane that contains a silicon atom-bonded hydrogen atom and a hydrocarbon compound or organic silicon compound having a plurality of aliphatic double bonds in the molecule to an addition reaction by means of a hydrosilylation reaction.

For example, it is possible to obtain the organic silicon compound by subjecting an organosiloxane that contains a silicon atom-bonded hydrogen atom, which is represented by the structural formula given below, and an organic silicon compound having an aliphatic double bond and a trialkylsilyl group in the molecule, which is selected from among 3-methacryloxypropyltris(trimethylsiloxy)silane, 3-methacryloxypropylmethylbis(trimethylsiloxy)silane, 3-methacryloxypropylmethoxybis(trimethylsiloxy)silane, 3-methacryloxypropylmethoxybis(trimethylsiloxy)silane, 3-acryloxypropyltrimethoxysilane, 3-acryloxypropyltris(trimethylsiloxy)silane, 3-acryloxypropylmethylbis(trimethylsiloxy)silane, 3-acryloxypropylmethoxybis(trimethylsiloxy)silane and 3-acryloxypropylmethoxybis(trimethylsiloxy)silane, to an addition reaction by means of a hydrosilylation reaction.

[Formula 6]

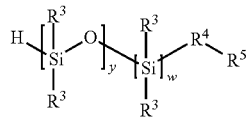

(In the formula, $R^3$, $R^4$ and $R^5$ are synonymous with those mentioned above, and y and w are synonymous with the values mentioned above)

Furthermore, as a method that does not involve the use of a hydrosilylation reaction, it is possible to subject an organic silicon compound and an organosiloxane that contains a silicon atom-bonded hydroxyl group to a substitution reaction.

Hydrosilylation reactions are generally carried out using a metal complex catalyst, but the production method of the present invention is not particularly limited in this respect. The catalyst used in the production method of the present invention is a catalyst that facilitates a reaction in which a silicon atom-bonded hydrogen atom is added to an aliphatic double bond, and is, for example, a catalyst based on a transition metal from group VIII of the periodic table, and preferably a platinum-based catalyst, specific examples of which include chloroplatinic acid, alcoholic solutions of chloroplatinic acid, platinum-olefin complexes, platinum-alkenylsiloxane catalysts and platinum-carbonyl complexes.

In the production method of the present invention, the molar ratio of the organosiloxane having a silicon atom-bonded hydrogen atom to the hydrocarbon compound or organic silicon compound having a plurality of aliphatic double bonds in the molecule is not particularly limited, but it is preferable for the reaction to be carried out in such a way that the quantity of the hydrocarbon compound or organic silicon compound having a plurality of aliphatic double bonds in the molecule is 0.5 to 1.5 moles, and more preferably 0.95 to 1.1 moles, relative to 1 mole of the organosiloxane having a silicon atom-bonded hydrogen atom.

In addition, the use of an organic solvent is optional in the production method of the present invention. Examples of this organic solvent include aromatic organic solvents such as benzene, toluene and xylene; aliphatic organic solvents such as pentane, hexane, heptane, octane and decane; ether-based organic solvents such as tetrahydrofuran, diethyl ether and dibutyl ether; ketone-based organic solvents such as acetone and methyl ethyl ketone; and ester-based organic solvents such as ethyl acetate and butyl acetate.

In addition, the reaction temperature is not particularly limited in the production method of the present invention, but the reaction may be carried out either at room temperature or under heating. In cases where the reaction is carried out under heating, it is preferable for the reaction temperature to be 50 to 200° C. In addition, the progress of the reaction can be determined by analyzing the reaction solution by means of a method such as gas chromatography analysis, infrared spectroscopy analysis or nuclear magnetic resonance analysis, and can be tracked by determining the quantity of raw materials remaining in the reaction system or the content of silicon atom-bonded hydrogen atoms or aliphatic unsaturated groups in the reaction system. Following completion of the reaction, the target organic silicon compound can be obtained by removing unreacted components and organic solvents.

In addition, a method for reacting a siloxane having a hydroxyl group at one terminal with an organic silicon compound having a single hydrolyzable group and a substituent group having a plurality of aromatic functional groups can be given as one example of a method for producing the organic silicon compound of the present invention.

The organic silicon compound of the present invention is useful as a surface treatment agent for a variety of functional fillers (and especially thermally conductive fillers), as mentioned above, but can also be used as a matrix component in a variety of resin compositions (and especially thermally-conductive silicone compositions). In such cases, it is possible to obtain a resin composition, and especially a thermally conductive silicone composition, having a relatively low viscosity and excellent handleability. In particular, in cases where the organic silicon compound of the present invention has one or more functional groups able to undergo a condensation reaction (for example, an alkoxy group) or functional groups able to undergo a hydrosilylation reaction (for example, an alkenyl group) in the molecule, the organic silicon compound can be used not only as a surface treatment agent, but also as all or a part of a primary component of a variety of functional resin compositions. For example, as a curable silicone resin composition, it is possible to add the aforementioned organopolysiloxane having one or more functional groups able to undergo a condensation reaction or functional groups able to undergo a hydrosilylation reaction in the molecule, a reactive silicone that acts as a crosslinking agent, a variety of functional fillers, which are described later, and a curing reaction catalyst, treat the surface of the functional filler in-situ (an integral blending method), and then cure the entire composition. In particular, the organic silicon compound of the present invention exhibits excellent blending stability with respect to a silicone resin composition (hereinafter referred to simply as a "silicone composition"), and therefore exhibits excellent dispersibility of a functional filler in a cured product and thermal stability when subjected to the above-mentioned curing reaction, and even if large quantities of these functional fillers are blended, it is possible to obtain a cured product or non-curable composition in which the cured product as a whole exhibits excellent and uniform functionality, and it is also possible to obtain a composition which has a relatively low viscosity and in which the viscosity of the composition as a whole is not especially high.

The organic silicon compound of the present invention exhibits excellent thermal stability and can improve the surface hydrophobicity, microdispersibility and dispersion stability of a fine member having a finely particulate or highly divided structure, and in cases where the organic silicon compound of the present invention is used to surface treat a variety of functional fillers in particular, a deterioration in handleability, such as gelling or a significant increase in viscosity, does not occur even if these fillers are filled at a high density in a resin composition. Therefore, by using the organic silicon compound of the present invention in a surface treatment agent, it is possible to fill a variety of functional fillers at a high density in a resin composition and obtain a resin composition having high performance and excellent handleability, which was not possible with conventional publicly known surface treatment agents due to high filling densities and stable dispersion being impossible to achieve. In particular, the organic silicon compound of the present invention can be used as a component of surface treatment agents for thermally conductive fillers. In such cases, a composition that contains a thermally conductive filler that has been treated with the surface treatment agent of the present invention exhibits excellent thermal stability and hardly suffers from gelling or an increase in viscosity. An explanation will now be given of uses of surface treatment agents that contain the organic silicon compound of the present invention.

The surface treatment agent of the present invention contains the organic silicon compound described above and particularly preferably contains at least 50 mass % of the organic silicon compound described above as the primary agent. However, the surface treatment agent of the present invention can be used by being diluted with a conventional publicly known solvent or the like, and other additives, such as antioxidants, anti-aging agents, pigments, dyes, other organic silicon compounds such as silane coupling agents and silylating agents, organic titanate compounds, organic aluminate compounds, organic tin compounds, waxes, fatty acids, fatty acid esters, fatty acid salts and silanol condensation catalysts such as organic tin compounds, can be added to the surface treatment agent of the present invention at levels that do not impair the objective of the present invention. Examples of other surface treatment compounds contained in the surface treatment agent of the present invention include silane compounds such as methyl(trimethoxy)silane, ethyl(trimethoxy)silane, hexyl(trimethoxy)silane, decyl(trimethoxy)silane, vinyl(trimethoxy)silane, 2-[(3,4)-epoxycyclohexyl]ethyl(trimethoxy)silane, 3-glycidoxypropyl(trimethoxy)silane, 3-methacryloxypropyl(trimethoxy)silane, 3-methacryloxypropyl(trimethoxy)silane, 3-acryloxypropyl(trimethoxy)silane and 1-(trimethoxy)-3,3,3-trimethylsiloxane. In addition, the surface treatment agent of the present invention may contain other reactive silicone compounds at levels that do not impair the effect of the present invention.

The surface treatment agent of the present invention is useful in the treatment of various substrate surfaces, and the substrate to be treated is not particularly limited. Examples of base materials able to be surface treated, other than the various functional fillers mentioned later, include types of glass such as soda glass, heat-reflecting glass, glass for vehicles, glass for ships, glass for aircraft, glass for buildings, glass containers and glass tools; metal sheets of copper, iron, stainless steel, aluminum, zinc, and so on; types of paper such as fine paper and coarse paper; synthetic resin films of polyester resins, polycarbonate resins, polystyrene resins, acrylic resins, and so on; fibers and fabrics such as natural fibers and synthetic fibers; plastic base materials consisting of the aforementioned synthetic resins; and materials such as pottery and ceramics.

Furthermore, the surface treatment agent of the present invention is useful as a surface treatment agent for a variety of functional fillers, and can improve the surface properties of a variety of functional fillers, for example hydrophobicity, cohesive properties, fluidity, dispersibility in, and compatibility with, polymers, and especially curable resins. These functional fillers are not particularly limited, but the surface treatment agent of the present invention has the advantages of being able to be used particularly advantageously to treat the surface of one or more types of filler selected from among thermally conductive fillers, fluorescent fillers, electrically conductive fillers, dielectric fillers, insulating fillers, light-diffusing fillers, translucent fillers, coloring fillers and reinforcing fillers, and improving the desired function with no deterioration in handleability, such as a significant increase in viscosity, even when these fillers are filled at a high density in a resin composition. In such cases, the form (spherical, rod-like, needle-like, lamellar, monolithic, spindle-like, cocoon-like, and so on), particle diameter (aerosol-like, finely particulate, pigment grade, and so on) and particle structure (crystalline, porous, non-porous, and so on) of the functional filler is not limited in any way, but it is preferable for the average primary particle diameter of the filler to fall within the range 1 nm to 100 μm. Moreover, the form and average primary particle diameter of the functional filler can be selected as appropriate according to the intended use and function of the filler, and the use of functional fillers having a plurality of average primary particle diameters and so on in order to improve the filling rate is encompassed by a preferred mode of the present invention.

Methods for treating the surface of such functional fillers include a method involving spraying a surface treatment agent or a solution (including a dispersion in an organic solvent or the like) thereof at a temperature between room temperature and 200° C. while stirring the functional filler with a stirrer, and then drying; a method involving mixing a functional filler and a surface treatment agent or a solution thereof with a stirrer (including a pulverizer such as a ball mill or jet mill or an ultrasonic wave disperser), and then drying; and a method involving mixing a treatment agent with a solvent, dispersing a functional filler in the mixture so as to adsorb the treatment agent on the surface of the filler, drying and then sintering. Furthermore, another example is a method involving adding a functional filler and a surface treatment agent to a resin in which the functional filler is to be blended, and then carrying out in-situ treatment (an integral blending method). When treating the surface of the functional filler, the quantity of surface treatment agent added is preferably 0.1 to 50 parts by mass, and more preferably 0.1 to 25 parts by mass, relative to 100 parts by mass of the functional filler.

In particular, fillers that can been advantageously treated by the surface treatment agent of the present invention include one or more types of filler selected from among inorganic fillers, organic fillers, nanocrystalline structures, quantum dots and fillers obtained by coating a silica layer on all or a part of the surface of these. In particular, these are already known as raw materials for thermally conductive materials, electrically conductive materials, semiconductor sealing materials, optical materials, functional coating materials, cosmetic materials, and so on, and the surface treatment agent of the present invention is suitable for treating the surface of these fillers, but by using the surface treatment agent of the present invention as a surface treatment agent for a filler in which all or a part of the surface of metal oxide fine particles having particle diameters of 1 to 500 nm is coated with a silica layer, it is possible to significantly improve the fine dispersibility and dispersion stability of the filler in a hydrophobic curable resin, and especially a silicone resin, and improve the functionality of the obtained curable resin.

Fillers able to be advantageously treated by the surface treatment agent of the present invention are inorganic fillers, with the thermally conductive fillers mentioned later being particularly preferred, but not limited thereto.

Fluorescent fillers are inorganic microparticles, nanocrystalline structures, quantum dots or the like which, when irradiated with ultraviolet or visible excitation light, emit fluorescent light having a wavelength longer than that of the excitation light, and the use of fluorescent microparticles having an excitation band in the wavelength region 300 to 500 nm and a luminescence peak within the wavelength region 380 to 780 nm, and the use of fluorescent microparticles that emit blue light (wavelength region: 440 to 480 nm), green light (wavelength region: 500 to 540 nm) yellow light (wavelength region: 540 to 595 nm) or red light (wavelength region: 600 to 700 nm), is particularly preferred. Examples of ordinary commercially available fluorescent microparticles include garnet-based microparticles such as YAG, other oxides, nitrides, oxynitrides, sulfides, oxysulfides and rare earth sulfides, rare earth-based aluminic acid chlorides activated mainly by a lanthanoid element such as Ce, such as $Y_3Al_5O_{12}$:Ce, $(Y,Gd)_3Al_5O_{12}$:Ce and $Y_3(Al, Ga)_5O_{12}$:Ce and halophosphoric acid chlorides. Specific examples of these fluorescent microparticles are, for example, the inorganic fluorescent microparticles disclosed in Japanese Unexamined Patent Application Publication No. 2012-052018.

Fluorescent microparticles treated using the surface treatment agent of the present invention generally have an average particle diameter of 0.1 to 300 μm, and may be treated in the form of a mixture of the fluorescent microparticles and a glass powder such as glass beads. Furthermore, the surface treatment agent can be used to treat a mixture consisting of a plurality of types of fluorescent microparticle, depending on the wavelength region of the excitation light or emitted light. For example, when obtaining white light by irradiating with ultraviolet excitation light, it is desirable to surface treat a mixture of fluorescent microparticles that emit blue, green, yellow and red florescent-light.

In the case of nanocrystalline structures, and especially semiconductor nanocrystalline structures, the wavelength of emitted light can be controlled according to the type of nanocrystal and the particle diameter by means of a quantum trapping effect, and in the case of semiconductor nanocrystals known as quantum dots in particular, the wavelength of emitted light can be controlled across the entire visible spectrum by controlling the particle diameter of nanocrystals, and nanocrystalline structures are therefore useful as optical materials such as light-emitting semiconductors, including LEDs, and especially radiating bodies and wavelength conversion materials that are used in place of light-emitting materials and fluorescent materials. These nanocrystalline structures consist of silicon-based nanocrystals, group II-VI compound semiconductor nanocrystals, group III-V compound semiconductor nanocrystals, group IV-VI compound semiconductor nanocrystals and mixtures thereof, and group II-VI compound semiconductor nanocrystals, such as CdSe semiconductors, group III-V compound semiconductor nanocrystals, such as GaN semiconductors, and group IV-VI compound semiconductor nanocrystals, such as SbTe semiconductors, are used in particular. These semiconductor nanocrystals may be obtained by vapor phase growth at high temperatures, but may also be colloidal semiconductor nanocrystals synthesized by means of an organic chemistry-based method (including a liquid phase method). In addition, the semiconductor nanocrystals may have a core-shell type structure.

The average particle size of the nanocrystal structures used in a light-emitting semiconductor—quantum dots, in particular—is within the range of approximately 0.1 nm to several 10 s of nm and is selected in accordance with the light emission wavelength. By subjecting these nanocrystals to surface treating with the surface treatment agent of the present invention, the organopolysiloxane orients or bonds to the surface of the nanocrystals, thereby preventing aggregation of the nanocrystals, improving the fine dispersibility and dispersion stability of the nanocrystals, and enabling a further improvement in the emission characteristics and light take out efficiency in a curable resin.

Electrically conductive fillers are components that are used in order to impart electrical conductivity to a composition, examples of which include various forms of carbon black; powdered metals such as silver, copper, iron and aluminum; metal oxides such as zinc oxide or tin oxide; and electrically conductive fillers obtained by coating a core material such as barium sulfate or titanium oxide with these materials. In addition, a variety of surfactants may be blended as auxiliary electrical conductivity-imparting agents, and these may be used in combination. Moreover, some of these are components that also function as thermally conductive fillers.

Dielectric fillers include ferroelectric fillers, paraelectric fillers and combinations thereof, and can impart a relatively high dielectric constant so as to enable a composition to store an electric charge. Examples of these dielectric fillers include lead titanate zirconate, barium titanate, calcium metaniobate, bismuth metaniobate, iron metaniobate, lanthanum metaniobate, strontium metaniobate, lead metaniobate, lead metatantalate, strontium barium titanate, sodium barium niobate, potassium barium niobate, rubidium barium niobate, titanium oxide, tantalum oxide, hafnium oxide, niobium oxide, aluminum oxide and steatite. Treating barium titanate and titanium oxide is particularly preferred from the perspective of improving the dielectric constant, but dielectric fillers are not limited to these.

Insulating fillers are used to impart a composition with electrical insulating properties, and can be the thermally conductive fillers mentioned later or fumed silica, precipitated silica or fused silica. Moreover, some or all of these are components that also function as reinforcing fillers.

Light-diffusing fillers are used to impart light-diffusing properties to a composition, and can be calcium carbonate, barium carbonate, crosslinked poly(methyl methacrylate) resin particles, silicone resin particles, polyorganosilsesquioxane particles, silica particles, quartz particles, silica fibers, quartz fibers, glass fibers, and so on. These light-diffusing fillers are used in applications such as optical elements, such as light-diffusing sheets in the field of liquid crystal displays, optical lenses and light guide plates, and glass replacement products, such as covers for street lights and laminated glasses for vehicles and buildings, and spherical silicone particles and the like can also be advantageously used in order to achieve a wrinkle-concealing effect (a soft focus effect) in cosmetic products.

Translucent fillers are microparticles having a high refractive index and having such a small size that light scattering can be ignored, and can be used to impart a high refractive index and high translucency to a composition. The surface treatment agent of the present invention can be advantageously used to surface treat metal oxide microparticles used in optical materials. The average particle diameter of metal oxide microparticles used as translucent fillers is 1 to 500 nm, preferably 1 to 100 nm, and more preferably 1 to 20 nm from the perspective of the translucency of optical materials that contain the particles. Furthermore, it is possible, and preferable, for these metal oxide microparticles to be nanocrystalline particles having a crystal grain diameter of 10 to 100 nm in order to improve the optical, electromagnetic and mechanical properties of an optical material. In addition, a translucent filler that has been treated with the surface treatment agent of the present invention has the advantage of exhibiting excellent heat resistance and hardly undergoing yellowing or discoloration when used in a semiconductor element or the like.

Examples of metal oxide microparticles include barium titanate, zirconium oxide, aluminum oxide (alumina), silicon oxide (silica), titanium oxide, strontium titanate, barium titanate zirconate, cerium oxide, cobalt oxide, indium tin oxide, hafnium oxide, yttrium oxide, tin oxide, niobium oxide and iron oxide. From the perspectives of optical and electrical properties, metal oxides containing one or more metal elements selected from among titanium, zirconium and barium are particularly preferred. Moreover, some of these are components that also function as thermally conductive fillers, dielectric fillers or reinforcing fillers.

In particular, zirconium oxide has a relatively high refractive index (2.2), and is therefore useful in applications such as optical materials that require a high refractive index and high translucency. Similarly, barium titanate has a high dielectric constant and a high refractive index, and is useful for improving the optical and electromagnetic performance of organic materials. By surface treating metal oxide microparticles such as barium titanate, the surface treatment agent of the present invention enables the metal oxide microparticles to be finely and stably dispersed in a hydrophobic curable resin, and enables the treated metal oxide microparticles to be stably blended at a higher quantity than untreated microparticles. This results in the advantage of a significant improvement in the optical properties (in particular, an increase in refractive index) and electromagnetic properties of an obtained resin composition.

Reinforcing fillers are components that impart high mechanical strength, which may be required according to intended uses of a composition. Examples of such reinforcing fillers include fumed silica, precipitated silica, fused silica and fumed titanium oxide. Moreover, these reinforcing fillers may be fillers obtained by hydrophobizing the surface thereof with a polyorganosiloxane other than the organopolysiloxane of the present invention or hexamethyldisilazane. From the perspective of improving mechanical strength in particular, the use of a reinforcing filler having a BET specific surface area of 130 $cm^2/g$ or higher is preferred.

In addition, the surface treatment agent of the present invention can be used to treat a conventionally known reinforcing filler that is a base material used in a functional resin composition. Examples of reinforcing fillers include talc, clay, mica powder, glass powder (glass beads), glass frits, glass cloth, glass tape, glass mats, and materials obtained by coating some or all of the surface of these materials with a silica layer.

When used to surface treat a swellable layered clay material, and especially a nanoclay material, that is blended in a functional resin composition in order to improve the mechanical properties, gas permeability or water vapor permeability thereof, the surface treatment agent of the present invention has the advantage of being able to improve the mechanical strength, gas permeability and water vapor permeability of the resin composition without impairing the dispersion stability or the quantities of other fillers able to be blended. Here, "nanoclay" means natural, synthetic, modified or unmodified ionic phyllosilicates primarily having a layered structure, examples of which include smectite clay minerals, for example montmorillonite, and especially sodium montmorillonite; and phyllosilicate-containing smectite and hectorite clays such as bentonite, hectorite, saponite, stevensite and beidellite. Because the layered structure of nanoclays is of the nano-order and extends in one direction only, interlaminar detachment or swelling readily occurs, it is possible to separate layers when incorporated in a resin composition, and it is preferable for peeling layers to have a thickness of less than 25 Å (approximately 2.5 nm), more preferably less than 10 Å (approximately 1 nm), and most preferably 5 to 8 Å (approximately 0.5 to 0.8 nm), and an aspect ratio (length/thickness) in excess of 10:1.

Furthermore, the surface treatment agent of the present invention can be used when carrying out a synthetic process or post-treatment step on a material obtained by coating some or all of the surface of these functional fillers with a silica layer. The method for using the surface treatment agent of the present invention in a synthetic process or post-treatment step is not limited particularly, but an example of a solid phase method is one involving treating the surface of a material obtained by coating some or all of the surface of these functional fillers with a silica layer by means of the above-mentioned method using the surface treatment agent according to the present invention prior to finely dividing the material, and then dispersing or pulverizing the material by using mechanical forces, ultrasonic waves, and so on. As the apparatus used for the dispersing or pulverizing, an already known means can be used without limitation.

Moreover, the above-mentioned functional fillers can be coated with a silica layer using a conventionally known method, examples of which include a method involving dispersing these finely divided materials in a suitable solvent and then adding an aqueous solution of sodium silicate under acidic conditions, a method involving adding a solution of silicic acid, or a method involving hydrolyzing a hydrolyzable tetrafunctional silane compound in the presence of an acidic or basic catalyst.

Meanwhile, the surface treatment agent of the present invention can be used when synthesizing a functional filler by means of a liquid phase method. When the surface treatment agent of the present invention is used in a liquid phase synthesis method, some or all of the surface of particles of the obtained functional filler is coated with the organopolysiloxane according to the present invention, which leads to the advantage of being able to achieve fine and uniform dispersion in a re-dispersion step and the advantage of being able to design the surface properties of the obtained finely divided material according to need by selecting the refractive index of the organic silicon compound or the type of reactive functional group. Furthermore, carrying out liquid phase synthesis in the presence of the surface treatment agent of the present invention leads to the advantage of being able to synthesize a variety finely divided materials, such as metal nanoparticles, semiconductor nanoparticles, core-shell type nanoparticles, nanorods and nanoplates, that are surface treated at the point of synthesis in an integrated process.

In cases where the organic silicon compound of the present invention or a filler that has been surface treated with the aforementioned organic silicon compound is blended in a variety of resin compositions, it is possible to achieve the advantages of being able to blend large quantities of a variety of functional fillers in the resin compositions without impairing handleability or dispersion stability and being able to obtain resin compositions in which these functional fillers are stably blended at high densities. An explanation will now be given of these resin compositions.

The resin portion that constitutes the resin composition can be blended with the organic silicon compound of the present invention without impairing the applicability thereof, and the resin portion is not particularly limited as long as the aforementioned variety of functional fillers can be supported or dispersed, and is preferably a resin that exhibits thickening properties, curing properties or phase change properties.

Here, thickening properties means that the initial viscosity does not greatly change, but that the overall viscosity increases when the composition is heated under prescribed usage conditions or when a thickening agent is used, thereby obtaining a gel, viscous liquid or paste, and an example thereof is a grease composition or the like.

Curing properties mean that the composition is cured by means of heating and so on, and examples thereof include hard coat resin compositions, semiconductor sealing resin compositions, resin compositions able to be molded into sheets, resin compositions that are cured into soft gels, and semi-curable resin compositions that form soft rubbers having a degree of plasticity.

Phase change properties mean that when the functional filler is filled in a heat-softenable resin having a softening point, such as a wax, phase change occurs according to the operating temperature of a heat-dissipating electronic component or the like, and an example thereof is what is called phase change material.

This type of resin component is not particularly limited, and examples thereof include hydrocarbon-based resins such as polyethylene, polypropylene, polymethylpentene, polybutene, crystalline polybutadiene, polystyrene and styrene-butadiene resins; vinyl-based resins such as poly(vinyl chloride) and poly(vinyl acetate); acrylic resins such as poly(methyl methacrylate); poly(vinylidene chloride); polytetrafluoroethylene; ethylene-polytetrafluoroethylene resins;

ethylene-vinyl acetate resins; acrylonitrile-styrene (AS) resins; acrylonitrile-butadiene-styrene (ABS) resins; acrylonitrile-acrylate-styrene (AAS) resins; acrylonitrile-poly(ethylene chloride)-styrene (ACS) resins; ionomers; polyacetals of yarns having linear structures (engineering plastics); polyamides (nylons); polycarbonates; poly(phenylene oxide); polyethylene terephthalate); poly(butylene terephthalate); polyarylates; polysulfones; polyether sulfones; polyimides; polyamideimides; polyether ether ketones; poly(phenylene sulfide); unsaturated polyesters; phenolic resins; epoxy resins; modified melamine resins; fluorine-based resins; silicone resins; cellulose-based resins such as celluloid, cellophane, cellulose acetate and cellulose acetate butyrate; resins derived from natural rubber, such as ebonite; and resins derived from proteins, such as gelatin.

The resin used in the present invention is preferably a resin composition that contains at least one type of resin selected from among the group consisting of heat-softenable resins such as waxes, epoxy resins, phenolic resins, silicone resins, melamine resins, urea resins, unsaturated polyester resins, diallyl terephthalate resins, poly(phenylene oxide) resins, polyimide resins, polyamide resins, (meth)acrylic acid ester-based resins, benzocyclobutene-based resins, fluorine-based resins, polyurethane-based resins, polycarbonate-based resins, norbornene-based resins, polyolefin-based resins and polystyrene-based resins. It is particularly preferable for the resin composition of the present invention to be a silicone composition.

These resin compositions may be curable resin compositions, thermoplastic resin compositions, or non-curable or thickenable resin compositions. In addition, in cases where the resin is a heat-softenable resin, the resin may be a phase change material. The resin composition of the present invention can be used in a variety of applications, depending on the type of functional filler and resin, but can be used in particular in applications selected from among thermally conductive materials, electrically conductive materials, semiconductor sealing materials, optical materials, functional coating materials and cosmetic materials.

It is particularly preferable for the organic silicon compound of the present invention and a filler obtained by treating the surface thereof with the aforementioned organic silicon compound to be blended in a silicone composition, and by using the organic silicon compound of the present invention for surface treatment of a thermally conductive filler in particular, it is possible to achieve good handleability with no increase in the viscosity of the composition even when the thermally conductive filler is filled in the resin composition at a high density in order to achieve high thermal conductivity, and in the case of a curable composition, it is possible to obtain a uniform cured product. An explanation will now be given of the surface treatment of a thermally conductive filler, which is the most preferred use of the organic silicon compound of the present invention, and of a thermally conductive silicone composition.

The thermally conductive silicone composition of the present invention contains (A) the aforementioned organopolysiloxane represented by the formula (1) and (B) a thermally conductive filler, and (A) the surface treatment of the thermally conductive filler by the aforementioned organopolysiloxane represented by the formula (1) is the same as that described above for the surface treatment of the aforementioned functional fillers. A resin composition containing a thermally conductive filler that has been subjected to surface treatment with the surface treatment agent of the present invention exhibits excellent thermal stability and hardly suffers from gelling or an increase in viscosity.

Component (B) in the thermally conductive silicone composition of the present invention is a thermally conductive filler that is used to impart the thermally conductive silicone composition with thermal conductivity, and is preferably one or more types of powder and/or fiber selected from among the group consisting of pure metals, alloys, metal oxides, metal hydroxides, metal nitrides, metal carbides, metal silicides, carbon, soft magnetic alloys and ferrites. It is particularly preferable to incorporate a carbonaceous material which contains no surface hydroxyl groups and which can be expected to exhibit interactions with aromatic groups or to incorporate a thermally conductive material having a lamellar appearance. These powders and/or fibers may be used after being treated with a variety of surface treatment agents known as coupling agents.

Examples of the pure metal include bismuth, lead, tin, antimony, indium, cadmium, zinc, silver, copper, nickel, aluminum, iron and metallic silicon. Examples of the alloy include alloys consisting of two or more metals selected from among the group consisting of bismuth, lead, tin, antimony, indium, cadmium, zinc, silver, copper, nickel, aluminum, iron and metallic silicon. Examples of the metal oxide include alumina, zinc oxide, silicon oxide, magnesium oxide, beryllium oxide, chromium oxide and titanium oxide. Examples of the metal nitride include boron nitride, aluminum nitride and silicon nitride. Examples of the metal carbide include silicon carbide, boron carbide and titanium carbide. Examples of the metal silicide include magnesium silicide, titanium silicide, zirconium silicide, tantalum silicide, niobium silicide, chromium silicide, tungsten silicide and molybdenum silicide. Examples of the carbon include diamond, graphite, a fullerene, carbon nanotubes, graphene, activated carbon and monolithic carbon black. Examples of the soft magnetic alloy include Fe—Si alloys, Fe—Al alloys, Fe—Si—Al alloys, Fe—Si—Cr alloys, Fe—Ni alloys, Fe—Ni—Co alloys, Fe—Ni—Mo alloys, Fe—Co alloys, Fe—Si—Al—Cr alloys, Fe—Si—B alloys and Fe—Si—Co—B alloys. Examples of the ferrite include Mn—Zn ferrites, Mn—Mg—Zn ferrites, Mg—Cu—Zn ferrites, Ni—Zn ferrites, Ni—Cu—Zn ferrites and Cu—Zn ferrites. It is preferable for component (B) to be one or more types of powder and/or fiber selected from among these.

It is preferable for the thermally conductive filler (B) to be (B1) a lamellar boron nitride powder having an average particle diameter of 0.1 to 30 μm, (B2) a granular boron nitride powder having an average particle diameter of 0.1 to 50 μm, (B3) a spherical and/or crushed aluminum oxide powder having an average particle diameter of 0.01 to 50 μm, (B4) a spherical and/or crushed graphite having an average particle diameter of 0.01 to 50 μm, or a mixture of two or more types thereof.

Examples of the form of the component (B) include spherical, needle-like, disc-like, rod-like, flat, monolithic and fibrous.

Examples of the surface treatment agent used to treat the powders and/or fibers of component (B) include surfactants, silane coupling agents, aluminum-based coupling agents and silicone-based surface treatment agents.

The content of component (B) in the present composition is not particularly limited, but in order to form a silicone composition having good thermal conductivity is preferably 30 vol. % or more, further preferably 30 to 90 vol. %, furthermore preferably 60 to 90 vol. %, and moreover preferably 80 to 90 vol. %, of the present composition. Similarly, in order to form a silicone composition having good thermal conductivity, the content of the component (B) is preferably 50 mass % or higher, more preferably 70 to 98 mass %, and particularly preferably 90 to 97 mass %, of the present composition.

Specifically, the content of the component (B) is preferably 100 to 3,500 parts by mass, further preferably 100 to 2,500 parts by mass, and further more preferably 100 to 2,500 parts by mass, relative to a total of 100 parts by mass of the component (A) and component (C). This is because the thermal conductivity of the obtained silicone composition tends to be insufficient if the content of the component (B) is lower than the lower limit of the aforementioned range, and if the content of the component (B) exceeds the upper limit of the aforementioned range, the viscosity of the obtained silicone composition becomes too high, meaning that the component (B) cannot be uniformly dispersed in the obtained a silicone composition or the handleability of the silicone composition tends to significantly deteriorate.

The organopolysiloxane of the component (C) in the thermally conductive silicone composition of the present invention is not particularly limited, but it is possible to use an organopolysiloxane having a hydrolyzable functional group, such as an alkoxy group, an alkoxyalkoxy group, an alkenoxy group or a trialkoxysilylalkyl group, bonded to a silicon atom in the molecule.

In addition, it is possible for the component (C) to be an organopolysiloxane having a monovalent hydrocarbon group having an aliphatic unsaturated bond bonded to a silicon atom in the molecule, an organopolysiloxane having a hydrogen atom bonded to a silicon atom in the molecule, or an organopolysiloxane having a hydrolyzable group bonded to a silicon atom in the molecule.

In the organopolysiloxane having at least 1 monovalent hydrocarbon group having an aliphatic unsaturated bond bonded to a silicon atom in the molecule, the monovalent hydrocarbon group having an aliphatic unsaturated bond is preferably a straight chain alkenyl group, and particularly preferably a vinyl group, an allyl group or a hexenyl group. In addition, an example of a group bonded to a silicon atom other than a monovalent hydrocarbon group having an aliphatic unsaturated bond is a monovalent hydrocarbon group not having an aliphatic unsaturated bond, and a preferred example thereof is an alkyl group or an aryl group, with an alkyl group having 1 to 4 carbon atoms being more preferred and a methyl group or ethyl group being particularly preferred. The viscosity at 25° C. of this organopolysiloxane is not particularly limited, but is preferably 20 to 100,000 mPas, more preferably 50 to 100,000 mPas, further preferably 50 to 50,000 mPas, and particularly preferably 100 to 50,000 mPas. The molecular structure of this organopolysiloxane is not particularly limited, and is, for example, a straight chain, branched chain, partially branched straight chain, cyclic or dendritic (dendrimer-like). Examples of this organopolysiloxane include homopolymers having these molecular structures, copolymers consisting of these molecular structures, and mixtures thereof.

Examples of this type of organopolysiloxane include dimethylpolysiloxanes capped at both molecular terminals with dimethylvinylsiloxy groups, dimethylpolysiloxanes capped at both molecular terminals with methylphenylvinylsiloxy groups, dimethylsiloxane-methylphenylsiloxane copolymers capped at both molecular terminals with dimethylvinylsiloxy groups, dimethylsiloxane-methylvinylsiloxane copolymers capped at both molecular terminals with dimethylvinylsiloxy groups, dimethylsiloxane-methylvinylsiloxane copolymers capped at both molecular terminals with trimethylsiloxy groups, methyl(3,3,3-trifluoropropyl) polysiloxanes capped at both molecular terminals with dimethylvinylsiloxy groups, dimethylsiloxane-methylvinylsiloxane copolymers capped at both molecular terminals with silanol groups, dimethylsiloxane-methylvinylsiloxane-methylphenylsiloxane copolymers capped at both molecular terminals with silanol groups, organosiloxane copolymers consisting of siloxane units represented by the formula $(CH_3)_3SiO_{1/2}$, siloxane units represented by the formula $(CH_3)_2(CH_2=CH)SiO_{1/2}$, siloxane units represented by the formula $CH_3SiO_{3/2}$ and siloxane units represented by the formula $(CH_3)_2SiO_{1/2}$, dimethylpolysiloxanes capped at both molecular terminals with silanol groups, dimethylsiloxane-methylphenylsiloxane copolymers capped at both molecular terminals with silanol groups, dimethylpolysiloxanes capped at both molecular terminals with trimethoxysiloxy groups, dimethylsiloxane-methylphenylsiloxane copolymers capped at both molecular terminals with trimethoxysilyl groups, dimethylpolysiloxanes capped at both molecular terminals with methyldimethoxysiloxy groups, dimethylpolysiloxanes capped at both molecular terminals with triethoxysiloxy groups, dimethylpolysiloxanes capped at both molecular terminals with trimethoxysilylethyl groups, and mixtures of two or more types thereof.

In an organopolysiloxane having 1 or more hydrogen atoms bonded to a silicon atom in the molecule, an example of a group bonded to a silicon atom other than a hydrogen atom is the aforementioned monovalent hydrocarbon group not having an aliphatic unsaturated bond, and a preferred example thereof is an alkyl group or an aryl group, with an alkyl group having 1 to 4 carbon atoms being more preferred and a methyl group or ethyl group being particularly preferred. The viscosity at 25° C. of this organopolysiloxane is not particularly limited, but is preferably 1 to 100,000 mPas, and particularly preferably 1 to 5,000 mPas. The molecular structure of this organopolysiloxane is not particularly limited, and is, for example, a straight chain, branched chain, partially branched straight chain, cyclic or dendritic (dendrimer-like). Examples of this organopolysiloxane include homopolymers having these molecular structures, copolymers consisting of these molecular structures, and mixtures thereof.

In an organopolysiloxane having a hydrolyzable group bonded to a silicon atom in the molecule, the hydrolyzable group is preferably an alkoxy group, an alkoxyalkoxy group, an alkenoxy group, an acyloxy group, a silanol group or a trialkoxysilylalkyl group.

Examples of this type of organopolysiloxane include dimethylpolysiloxanes capped at one molecular terminal with a trimethoxysiloxy group (a trimethylsiloxy group), dimethylpolysiloxanes capped at one molecular terminal with a trimethoxysiloxy group (a dimethylvinylsiloxy group), dimethylsiloxane-methylphenylsiloxane copolymers capped at one molecular terminal with a trimethoxysiloxy group (a dimethylvinylsiloxy group), dimethylpolysiloxanes capped at one molecular terminal with a trimethoxysiloxy group (a dimethylvinylsiloxy group), dimethylpolysiloxanes capped at both molecular terminals with trimethoxysiloxy groups, dimethylsiloxane-methylmethoxysiloxane copolymers capped at both molecular terminals with trimethylsiloxy groups, dimethylsiloxane-methylethoxysiloxane copolymers capped at both molecular terminals with trimethylsiloxy groups, methyl(3-trimethoxysilylpropyl)-dimethylsiloxane copolymers capped at both molecular terminals with trimethoxysiloxy groups, dimethylpolysiloxanes capped at both molecular terminals with dimethyl(5-trimethoxysilylhexyl) groups, dimethylpolysiloxanes capped at both molecular terminals with silanol groups, dimethylsiloxane-methylphenylsiloxane copolymers capped at both molecular terminals with silanol groups, dimethylpolysiloxanes capped at both molecular terminals with methyldimethoxysiloxy groups, dimethylpolysiloxanes capped at both molecular terminals with triethoxysiloxy groups, dimethylpolysiloxanes capped at both molecular terminals with trimethoxysilylethyl groups, and mixtures of two or more types thereof.

The method of preparing the thermally conductive silicone composition of the present invention is not particularly limited. For example, a preparation method [1] wherein the component (A) is mixed with the component (B), the component (C) is added in small amounts thereto, and the resulting composition is mixed may be used or, alternatively, a preparation method [2] wherein the component (A) is premixed with the component (C), and the component (B) is added in small amounts thereto may be used. However, the preparation method [1] is particularly preferable. A variety of apparatuses can be used as the mixing apparatus, but from the perspective of mixing efficiency, the use of a planetary mixer (commercially available as the "Awatori Rentaro" series manufactured by Thinky, the UM-118 manufactured by UNIX, the UFO series manufactured by EME and the Speed Mixer manufactured by Hauschild) is particularly preferred.

The surface treatment agent for a thermally conductive filler and thermally conductive silicone composition of the present invention may also contain a variety of additives, for example reinforcing materials such as fumed titanium oxide; non-reinforcing materials such as diatomaceous earth, aluminosilicates, iron oxide, zinc oxide and calcium carbonate; and materials obtained by surface treating these fillers with organic silicon compounds such as organosilanes and polyorganosiloxanes, as optional components at levels that do not impair the objective of the present invention. Additionally, as necessary, methyl ethyl ketone, methyl isobutyl ketone, or a similar solvent, a pigment, a dye, a heat-resistant agent, a flame retardant, an internal release agent, a plasticizer, a mineral oil, a nonfunctional silicone oil, or similar additive commonly used in silicone compositions may be compounded.

EXAMPLES

The present invention is described in detail below based on examples, but the present invention is not limited to the examples. Note that in the Examples, physical properties are values measured at 25° C. Moreover, Me represents a $CH_3$ group, Np represents a 2-naphthyl group, and Vi represents a vinyl group.

Practical Example 1

Synthesis of organic silicon compound represented by formula

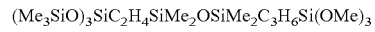

91.47 g (0.681 moles) of 1,1,3,3-tetramethyldisiloxane was placed in a 200 mL four-mouthed flask equipped with a stirrer, a thermometer, a condenser tube and a dropping funnel under a nitrogen atmosphere, stirred, and heated to 50° C. 43.7 g (0.1362 moles) of tris(trimethylsiloxy)vinylsilane and a complex of platinum and 1,3-divinyltetramethyldisiloxane were added and mixed so that the quantity of platinum metal was 5 ppm relative to the total mass of the reaction mixture, the obtained mixture was filled in a dropping funnel, and added dropwise while water cooling or air cooling the reaction mixture so that the temperature of the reaction liquid did not exceed 70° C. Following completion of the dropwise addition, the reaction liquid was stirred at 60° C. for 2 hours. The reaction mixture was analyzed by gas chromatography (hereinafter abbreviated to GLC), and the reaction was found to be complete due to the fact that the tris(trimethylsiloxy)vinylsilane peak had disappeared. 49.0 g (a yield of 79%) of a distillate was obtained by subjecting the reaction mixture to vacuum distillation at a temperature of 84 to 92° C. and a pressure of 1 hPa. When this distillate was analyzed using nuclear magnetic resonance (hereinafter abbreviated to NMR) and infrared spectroscopy (hereinafter abbreviated to IR), it was understood that this distillate was a silicon atom-bonded hydrogen atom-containing organosiloxane represented by the formula $(Me_3SiO)_3SiC_2H_4SiMe_2OSiMe_2H$. This siloxane had a purity of 90.6%, as measured by GLC.

Furthermore, 18.3 g (0.113 moles, purity 99%) of allyltrimethoxysilane and a complex of platinum and 1,3-divinyltetramethyldisiloxane were added and mixed in a 200 mL four-mouthed flask equipped with a stirrer, a thermometer, a condenser tube and a dropping funnel under a nitrogen atmosphere so that the quantity of platinum metal was 5 ppm relative to the total mass of the reaction mixture, and the mixture was then heated to 40° C. 49.0 g (0.107 moles) of the above-mentioned $(Me_3SiO)_3SiC_2H_4SiMe_2OSiMe_2H$ was added dropwise while water cooling or air cooling was performed on the reaction mixture so that the temperature of the reaction liquid did not exceed 70° C. Following completion of the dropwise addition, the reaction liquid was stirred at 60° C. for 2 hours, and when the reaction mixture was analyzed by IR, the reaction was found to be complete due to the fact that a SiH peak attributable to $(Me_3SiO)_3SiC_2H_4SiMe_2OSiMe_2H$ had disappeared. 60.0 g (a yield of 89%) of a reaction product was obtained by removing solvents, low boiling point reactants, and so on by heating the reaction mixture under reduced pressure at a temperature of 115° C. and a pressure of 1 hPa. When this distillate was analyzed using NMR and IR, it was understood that this distillate was an organic silicon compound represented by the formula $(Me_3SiO)_3SiC_2H_4SiMe_2OSiMe_2C_3H_6Si(OMe)_3$.

Practical Example 2

Synthesis of organic silicon compound represented by formula $(Me_3SiO)_3SiC_2H_4SiMe_2OSiMe_2C_2H_4Np$ 49.0 g (a yield of 79%) of this compound was obtained in the same way as in Practical Example 2, except that the allyltrimethoxysilane was replaced with 2-vinylnaphthalene. When this distillate was analyzed using NMR and IR, it was confirmed that this distillate was an organic silicon compound represented by the formula $(Me_3SiO)_3SiC_2H_4SiMe_2OSiMe_2C_2H_4Np$.

Practical Example 3

Synthesis of organic silicon compound represented by the average formula $(Me_3SiO)_3SiC_2H_4(SiMe_2O)_nSiMe_2C_3H_6Si(OMe)_3$
($n$(average)=15)

101.3 g (0.086 moles) of an organic silicon compound represented by the average formula $H(SiMe_2O)_nSiMe_2H$ (n (average)=15) was placed in a 200 mL four-mouthed flask equipped with a stirrer, a thermometer, a condenser tube and a dropping funnel under a nitrogen atmosphere, stirred, and heated to 50° C. 32.2 g (0.100 moles) of tris(trimethylsiloxy)vinylsilane, 16.2 g (0.100 moles) of allyltrimethoxysilane and a complex of platinum and 1,3-divinyltetramethyldisiloxane were added and mixed so that the quantity of platinum metal was 5 ppm relative to the total mass of the reaction mixture, the obtained mixture was filled in a dropping funnel, and added dropwise while water cooling or air cooling was performed on the reaction mixture so that the temperature of the reaction liquid did not exceed 70° C. Following completion of the dropwise addition, the reaction liquid was stirred at 60° C. for 2 hours. When the reaction mixture was analyzed using IR, the reaction was found to be complete due to the fact that a SiH peak attributable to $H(SiMe_2O)_nSiMe_2H$ (n (average)=15) had disappeared. The reaction mixture was heated under reduced pressure at a temperature of 115° C. and a pressure of 1 hPa to remove solvents, low boiling point reactants, and so on, so as to obtain 135.6 g (a yield of 95%) of a reaction product. When this distillate was analyzed using NMR and IR, it was understood that this distillate was a mixture containing an organic silicon compound represented by the average structural formula $(Me_3SiO)_3SiC_2H_4(SiMe_2O)_nSiMe_2C_3H_6Si(OMe)_3$
($n$(average)=15).

<Thermally Conductive Silicone Composition>

A thermally conductive silicone composition containing the organic silicon compound of the present invention will now be explained in detail. In addition, the viscosity and thermal conductivity of the thermally conductive silicone composition were measured as explained below.

[Viscosity of Thermally Conductive Silicone Composition]

The viscosity at 25° C. of the thermally conductive silicone composition was measured using a rheometer (AR550) manufactured by TA Instruments. Using parallel plates having diameters of 20 mm, measurements were carried out at a gap of 200 μm and a shear rate of 10.0 (1/s). A low viscosity value means that the thermally conductive silicone composition has a low viscosity and exhibits excellent handleability.

[Thermal Conductivity]

The thermal conductivity at 25° C. was measured using a C-Therm TCi thermal conductivity measuring apparatus manufactured by C-Therm.

Practical Example 4

A thermally conductive silicone composition was prepared by placing 35.0 vol. % of the organic silicon compound obtained in Practical Example 1, which is represented by the formula $(Me_3SiO)_3SiC_2H_4SiMe_2OSiMe_2C_3H_6Si(OMe)_3$, 48.7 vol. % of an alumina powder (Filler B-1) having an average particle diameter of 12 μm (AS-40 manufactured by Showa Denko Kabushiki Kaisha) and 16.3 vol. % of A boron nitride powder (Filler B-2) having an average particle diameter of 20 in a 100 mL container. In addition, the alumina powder and boron nitride with surface treated using an organic silicon compound represented by the formula $ViMe_2SiO(Me_2SiO)_{20}SROMe)_3$. This thermally conductive silicone composition was mixed for 30 seconds using an AR-100 planetary mixer manufactured by Thinky, then subjected to mixing by scraping, and then mixed for another 30 seconds. This thermally conductive silicone composition had a viscosity of 183 Pas (at a shear rate of 10.0 (1/s)) and a thermal conductivity of 4.3 W/mK.

Practical Example 5

A thermally conductive silicone composition was prepared in the same way as Practical Example 4, except that the organic silicon compound obtained in Practical Example 2, which is represented by a formula $(Me_3SiO)_3SiC_2H_4SiMe_2OSiMe_2C_2H_4Np$, was used as the organic silicon compound (A) instead of the organic silicon compound obtained in Practical Example 1. This thermally conductive silicone composition had a viscosity of 60 Pas (at a shear rate of 10.0 (1/s)) and a thermal conductivity of 3.7 W/mK.

Comparative Examples 1 and 2

Thermally conductive silicone compositions were prepared in the same way as in Practical Example 4, except that the organic silicon compounds shown in Table 1 were used as the organic silicon compound (A) instead of the organic silicon compound obtained in Practical Example 1. The viscosity (at a shear rate of 10.0 (1/s)) and thermal conductivity of each of these thermally conductive silicone compositions are shown in Table 1.

Practical Example 6

A thermally conductive silicone composition was prepared by placing 15.0 vol. % of the organic silicon compound obtained in Practical Example 3, which is represented by a formula $(Me_3SiO)_3SiC_2H_4(SiMe_2O)_nC_3H_6Si(OMe)_3$ (n (average)=15) and 85.0 vol. % of an alumina powder having an average particle diameter of 12 μm (AS-40 manufactured by Showa Denko Kabushiki Kaisha) in a 100 mL container. In addition, the used alumina powder was subjected to the surface treatment using an organic silicon compound represented by a formula $ViMe_2SiO(Me_2SiO)_mSi(OMe)_3$ (m (average)=200). This thermally conductive silicone composition was mixed for 30 seconds using an AR-100 planetary mixer manufactured by Thinky, then subjected to mixing by scraping, and then mixed for another 30 seconds. This thermally conductive silicone composition had a viscosity of 53 Pas (at a shear rate of 10.0 (1/s)) and a thermal conductivity of 6.9 W/mK.

Comparative Example 3

A thermally conductive silicone composition was prepared in the same way as in Practical Example 6, except that dimethylpolysiloxane-50cs (manufactured by Dow Corning Toray Silicone Co., Ltd.) was used as the organic silicon compound (A) instead of the organic silicon compound represented by a formula $(Me_3SiO)_3SiC_2H_4(SiMe_2O)_nSiMe_2C_3H_6Si(OMe)_3$ (n (average)=15). This thermally conductive silicone composition had a viscosity of 88 Pas (at a shear rate of 10.0 (1/s)) and a thermal conductivity of 6.9 W/mK.

The viscosity and thermal conductivity measurement results of the thermally conductive silicone compositions prepared in Practical Examples 4 to 6 and Comparative Examples 1 to 3 are shown in Table 1 below.

TABLE 1

|  | Practical Example 4 | Practical Example 5 | Comparative Example 1 | Comparative Example 2 | Practical Example 6 | Comparative Example 3 |
|---|---|---|---|---|---|---|
| Organic silicon compound (A) Vol. % | Practical Example 1 35.0 | Practical Example 2 35.0 | *1 35.0 | *2 35.0 | *3 35.0 | *4 35.0 |
| Filler (B-1) (Vol. %) | 48.7 | 48.7 | 48.7 | 48.7 | 85.0 | 85.0 |
| Filler (B-2) (Vol. %) | 16.3 | 16.3 | 16.3 | 16.3 | — | — |
| Viscosity (10.0 (1/s)) | 183 | 60 | 270 | >1000 | 53 | 88 |
| Thermal conductivity (W/mK) | 4.3 | 3.7 | 3.6 | 4.5 | 6.9 | 6.9 |

*1: $C_8H_{17}Me_2SiOMe_2SiC_2H_4Np$
*2: Dimethylpolysiloxane-300cs (manufactured by Dow Corning Toray Silicone Co., Ltd.)
*3: $(Me_3SiO)_3SiC_2H_4(SiMe_2O)_nSiMe_2C_3H_6Si(OMe)_3$ (n (average) = 15)
*4: Dimethylpolysiloxane-50cs (manufactured by Dow Corning Toray Silicone Co., Ltd.)
(B-1) Alumina powder (average particle diameter 40 μm)
(B-2) Boron nitride powder (average particle diameter 8 μm)

From the results shown in Table 1, it can be understood that Practical Examples 4 and 5, which used the organic silicon compounds obtained in Practical Examples 1 and 2, exhibited a lower viscosity than Comparative Examples 1 and 2 and a similar thermal conductivity. In addition, comparing the results of Practical Example 6 and Comparative Example 3, each of which contained 85 vol. % of a thermally conductive filler, it can be understood that Practical Example 6, which used the organic silicon compound obtained in Practical Example 3, exhibited a lower viscosity and similar thermal conductivity.

Practical Example 7

8.7 parts by mass of an organic silicon compound represented by the formula $(Me_3SiO)_3SiC_2H_4SiMe_2OSiMe_2C_4H_8CH=CH_2$, 8.1 parts by mass of an organopolysiloxane represented by the formula $CH_2=CH(CH_3)_2SiO[(CH_3)_2SiO]_pSi(CH_3)_2CH_2=CH$ (p (average)=300), 2.1 parts by mass of an organopolysiloxane represented by the formula $(CH_3)_3SiO[(CH_3)HSiO]_q$ $[(CH_3)_2 SiO]_rSi(CH_3)_3$ (q (average)=30, r (average)=30), 25.6 parts by mass of an alumina powder having an average particle diameter of 12 μm, 0.09 parts by mass of tetravinyltetramethylcyclotetrasiloxane and 0.9 parts by mass of a 1,3-divinyltetramethyldisiloxane-platinum complex containing 0.5 mass % of platinum were placed in a 100 mL container, mixed for 30 seconds using an AR-100 planetary mixer manufactured by Thinky, then subjected to mixing by scraping, and then mixed for another 30 seconds. A thermally conductive silicone cured product (having a thickness of 1 mm) was prepared by subjecting this composition to a hydrosilylation reaction by heating for 15 minutes at a temperature of 150° C. This thermally conductive silicone cured product had a thermal conductivity of 5.0 W/mK.

<Surface Treatment Agent for Thermally Conductive Filler>

A surface treatment agent for a thermally conductive filler, which contains the organic silicon compound of the present invention, will now be explained in detail. In addition, the viscosity of a thermally conductive silicone composition containing a thermally conductive filler that had been treated with the surface treatment agent of the present invention, was measured using the same method as that described above.

Practical Example 8

An alumina powder having an average particle diameter of 12 μm (AS-40 manufactured by Showa Denko Kabushiki Kaisha) was surface treated with the organic silicon compound obtained in Practical Example 1, which is represented by the formula

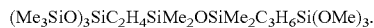

$(Me_3SiO)_3SiC_2H_4SiMe_2OSiMe_2C_3H_6Si(OMe)_3$.

Mixing and stirring was carried out for 1 minute at 3,000 rpm using a high speed mixing agitator, matter that had stuck to the inner walls was scraped off, and mixing and stirring was then carried out for another 1 minute at 3000 rpm.

A thermally conductive silicone composition was prepared by placing 26.2 vol. % of dimethylsiloxane-300cs and 73.8 vol. % of the surface treated alumina powder having an average particle diameter of 12 μm (AS-40 manufactured by Showa Denko Kabushiki Kaisha) in a 100 mL container. This thermally conductive silicone composition was mixed for 30 seconds using an AR-100 planetary mixer manufactured by Thinky, then subjected to mixing by scraping, and then mixed for another 30 seconds. This thermally conductive silicone composition was stored in an oven at 180° C., and the viscosity of the composition was measured immediately following preparation (0 hours), after 264 hours, and after 1224 hours. The results are shown in Table 2.

Comparative Examples 4 to 7

Thermally conductive silicone compositions were prepared in the same way as in Practical Example 8, except that the organic silicon compounds shown in Table 2 were used as the organic silicon compound used for the surface treatment instead of the organic silicon compound represented by the formula $(Me_3SiO)_3SiC_2H_4SiMe_2OSiMe_2C_3H_6Si(OMe)_3$. The viscosity of each of the thermally conductive silicone compositions was measured immediately following preparation (0 hours), after 264 hours, and after 1224 hours. The results are shown in Table 2.

TABLE 2

| | Practical Example 8 | Comparative Example 4 | Comparative Example 5 | Comparative Example 6 | Comparative Example 7 |
|---|---|---|---|---|---|
| Organic silicon compound (A) | Practical Example 1 | *5 | *6 | *7 | *8 |
| Viscosity (0 hours) (10.0 (1/s)) | 142 | 62 | 33 | 97 | 97 |
| Viscosity (264 hours) (10.0 (1/s)) | 148 | 95 | Gelling | 306 | Gelling |
| Viscosity (1224 hours) (10.0 (1/s)) | 215 | 108 | — | Gelling | — |

*5: $ViMe_2SiO(Me_2SiO)_{20}Si(OMe)_3$
*6: $C_{10}H_{21}SiMe_2OSiMe_2C_3H_6Si(OMe)_3$
*7: $Me_3SiO(SiMe_2)_{14}(SiMe((Me_3SiO)_3SiC_2H_4)O)_2SiMe(C_3H_6Si(OMe)_3)OSiMe_3$
*8: $Me_3SiO(SiMe_2)_{14}(SiMe(C_{10}H_{21})O)_2SiMe(C_3H_6Si(OMe)_3)OSiMe_3$

From the results shown in Table 2, it can be understood that Practical Example 8, which used the organic silicon compound obtained in Practical Example 1, exhibited a smaller increase in viscosity and better stability over time than Comparative Example 4. In addition, the thermally conductive silicone compositions obtained in Comparative Examples 5 to 7 underwent gelling.

Practical Example 9

A thermally conductive silicone grease having a filler content of 70 vol. % was prepared by placing 4.3 parts by mass of an organopolysiloxane represented by the formula $\{(CH_3)_3SiO\}_3SiC_2H_4(CH_3)_2SiOSi(CH_3)_2C_2H_4Np$ (Np represents a 2-naphthyl group), 79.6 parts by mass of alumina powder having an average particle diameter of 12 μm, 4.4 parts by mass of boron nitride having an average particle diameter of 20 μm, 8.8 parts by mass of boron nitride having an average particle diameter of 0.8 μm and 6.0 parts by mass of $(CH_3)_3SiO[(CH_3)_2SiO]_nSi(CH_3)_2C_2H_4Np$ (n (average)=25) in a 100 mL container. This thermally conductive silicone grease was mixed for 30 seconds using an AR-100 planetary mixer manufactured by Thinky, then subjected to mixing by scraping, and then mixed for another 30 seconds. This thermally conductive silicone composition had a viscosity of 120 Pas (at a shear rate of 10.0 (1/s)) and a thermal conductivity of 4.5 W/mK.

The invention claimed is:

1. A resin composition comprising an organic silicon compound and a filler whose surface has been treated therewith, wherein the organic silicon compound is represented by a formula (1) below:

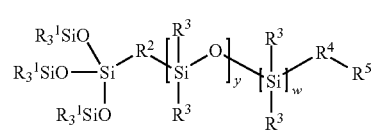

(1)

wherein each of $R^1$ and $R^3$ is a group selected independently from the group consisting of alkyl groups, alkenyl groups, aryl groups, aralkyl groups and alkoxy groups having 1 to 20 carbon atoms, $R^2$ is a divalent hydrocarbon group, which may optionally contain a hetero atom, or an oxygen atom, $R^4$ is a divalent hydrocarbon group, which may optionally contain a hetero atom, or a direct bond to a silicon (Si) atom, $R^5$ is a monovalent group represented by $(R^6O)_q R^7_{(3-q)}Si$ or a monovalent hydrocarbon group having 1 to 20 carbon atoms, and each of $R^6$ and $R^7$ is a group independently selected from the group consisting of alkyl groups, alkenyl groups, aryl groups, aralkyl groups and alkoxy groups having 1 to 20 carbon atoms, and q is an integer between 1 and 3, y is an integer between 0 and 200, and w is an integer that is 0 or 1.

2. A material comprising the resin composition according to claim 1, wherein the material is further defined as a thermally conductive material, an electrically conductive material, a semiconductor sealing material, an optical material, a functional coating material or a cosmetic material.

3. The resin composition according to claim 1, which exhibits thickening properties, curing properties or phase change properties.

4. A thermally conductive silicone composition comprising (A) an organic silicon compound and (B) a thermally conductive filler; wherein the organic silicon compound is represented by a formula (1) below:

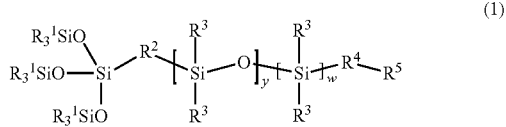

(1)

wherein each of $R^1$ and $R^3$ is a group selected independently from the group consisting of alkyl groups, alkenyl groups, aryl groups, aralkyl groups and alkoxy groups having 1 to 20 carbon atoms, $R^2$ is a divalent hydrocarbon group, which may optionally contain a hetero atom, or an oxygen atom, $R^4$ is a divalent hydrocarbon group, which may optionally contain a hetero atom, or a direct bond to a silicon (Si) atom, $R^5$ is a monovalent group represented by $(R^6O)_q R^7_{(3-q)}Si$ or a monovalent hydrocarbon group having 1 to 20 carbon atoms, and each of $R^6$ and $R^7$ is a group independently selected from the group consisting of alkyl groups, alkenyl groups, aryl groups, aralkyl groups and alkoxy groups having 1 to 20 carbon atoms, and q is an integer between 1 and 3, y is an integer between 0 and 200, and w is an integer that is 0 or 1.

5. The thermally conductive silicone composition according to claim 4, further comprising (C) at least one type of organopolysiloxane other than the organic silicon compound.

6. The thermally conductive silicone composition according to claim 4, wherein the thermally conductive filler (B) is at least one type of powder and/or fiber selected from the group consisting of a pure metal, an alloy, a metal oxide, a metal hydroxide, a metal nitride, a metal carbide, a metal silicide, carbon, a soft magnetic alloy and a ferrite.

7. The thermally conductive silicone composition according to claim 6,
wherein the pure metal is bismuth, lead, tin, antimony, indium, cadmium, zinc, silver, copper, nickel, aluminum, iron or metallic silicon,
wherein the alloy is an alloy consisting of two or more metals selected from the group consisting of bismuth, lead, tin, antimony, indium, cadmium, zinc, silver, copper, nickel, aluminum, iron and metallic silicon,
wherein the metal oxide is alumina, zinc oxide, silicon oxide, magnesium oxide, beryllium oxide, chromium oxide or titanium oxide,
wherein the metal hydroxide is magnesium hydroxide, aluminum hydroxide, barium hydroxide or calcium hydroxide,
wherein the metal nitride is boron nitride, aluminum nitride or silicon nitride,
wherein the metal carbide is silicon carbide, boron carbide or titanium carbide,
wherein the metal silicide is magnesium silicide, titanium silicide, zirconium silicide, tantalum silicide, niobium silicide, chromium silicide, tungsten silicide or molybdenum silicide,
wherein the carbon is diamond, graphite, a fullerene, carbon nanotubes, graphene, activated carbon or monolithic carbon black,
wherein the soft magnetic alloy is an Fe—Si alloy, an Fe—Al alloy, an Fe—Si—Al alloy, an Fe—Si—Cr alloy, an Fe—Ni alloy, an Fe—Ni—Co alloy, an Fe—Ni—Mo alloy, an Fe—Co alloy, an Fe—Si—Al—Cr alloy, an Fe—Si—B alloy or an Fe—Si—Co—B alloy, and
wherein the ferrite is a Mn—Zn ferrite, a Mn—Mg—Zn ferrite, a Mg—Cu—Zn ferrite, a Ni—Zn ferrite, a Ni—Cu—Zn ferrite or a Cu—Zn ferrite.

8. The thermally conductive silicone composition according to claim 4, wherein the thermally conductive filler (B) is (B1) a lamellar boron nitride powder having an average particle diameter of 0.1 to 30 μm, (B2) a granular boron nitride powder having an average particle diameter of 0.1 to 50 μm, (B3) a spherical and/or crushed aluminum oxide powder having an average particle diameter of 0.01 to 50 μm, (B4) a spherical and/or crushed graphite having an average particle diameter of 0.01 to 50 μm, or a mixture of two or more types thereof.

9. The thermally conductive silicone composition according to claim 5, wherein the content of component (B) is 100 to 3,500 parts by mass relative to a total of 100 parts by mass of component (A) and component (C).

10. The thermally conductive silicone composition according to claim 5, wherein the organopolysiloxane of component (C) has a hydrolyzable functional group bonded to a silicon atom in the molecule.

11. The thermally conductive silicone composition according to claim 5, wherein component (C) comprises 1) an organopolysiloxane having a monovalent hydrocarbon group having an aliphatic unsaturated bond bonded to a silicon atom in the molecule, and 2) an organopolysiloxane having a hydrogen atom bonded to a silicon atom in the molecule, wherein the composition contains a catalyst which thickens or cures these organopolysiloxanes by a hydrosilylation reaction.

12. The thermally conductive silicone composition according to claim 5, wherein component (C) comprises 1) an organopolysiloxane having a monovalent hydrocarbon group having an aliphatic unsaturated bond bonded to a silicon atom in the molecule, 2) an organopolysiloxane having a hydrogen atom bonded to a silicon atom in the molecule, and 3) an organopolysiloxane having a hydrolyzable functional group bonded to a silicon atom in the molecule, wherein the composition contains a catalyst which thickens or cures these organopolysiloxanes by a hydrosilylation reaction.

13. A gel or cured product obtained by thickening or curing the thermally conductive silicone composition according to claim 11.

14. A gel or cured product obtained by thickening or curing the thermally conductive silicone composition according to claim 12.

15. A method of preparing a surface treated filler, said method comprising:

treating a surface of a filler with an organo silicon compound to give the surface treated filler, wherein the organic silicon compound is represented by a formula (1) below:

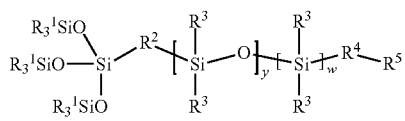
(1)

wherein each of $R^1$ and $R^3$ is a group selected independently from the group consisting of alkyl groups, alkenyl groups, aryl groups, aralkyl groups and alkoxy groups having 1 to 20 carbon atoms, $R^2$ is a divalent hydrocarbon group, which may optionally contain a hetero atom, or an oxygen atom, $R^4$ is a divalent hydrocarbon group, which may optionally contain a hetero atom, or a direct bond to a silicon (Si) atom, $R^5$ is a monovalent group represented by $(R^6O)_q R^7_{(3-q)}Si$ or a monovalent hydrocarbon group having 1 to 20 carbon atoms, and each of $R^6$ and $R^7$ is a group independently selected from the group consisting of alkyl groups, alkenyl groups, aryl groups, aralkyl groups and alkoxy groups having 1 to 20 carbon atoms, and q is an integer between 1 and 3, y is an integer between 0 and 200, and w is an integer that is 0 or 1.

16. A surface treated filler prepared in accordance with the method of claim 15.

17. The resin composition according to claim 1, wherein y in the formula (1) is an integer between 1 and 20.

18. The thermally conductive silicone composition according to claim 4, wherein y in the formula (1) is an integer between 1 and 20.

19. The method composition according to claim 15, wherein y in the formula (1) is an integer between 1 and 20.

* * * * *